(12) United States Patent
Pike, Jr. et al.

(10) Patent No.: US 7,207,989 B2
(45) Date of Patent: Apr. 24, 2007

(54) METHOD FOR ABLATING WITH NEEDLE ELECTRODE

(75) Inventors: Robert W. Pike, Jr., Coto de Caza, CA (US); John L. Sapp, Jr., Halifax (CA); William G. Stevenson, Needham, MA (US); Robert A. Mest, Long Beach, CA (US)

(73) Assignees: Biosense Webster, Inc., Diamond Bar, CA (US); The Brigham & Women's Hospital, Inc., Boston, MA (US)

( * ) Notice: Subject to any disclaimer, the term of this patent is extended or adjusted under 35 U.S.C. 154(b) by 185 days.

(21) Appl. No.: 10/694,118

(22) Filed: Oct. 27, 2003

(65) Prior Publication Data

US 2005/0090818 A1     Apr. 28, 2005

(51) Int. Cl.
*A61B 18/18* (2006.01)
(52) U.S. Cl. .............. 606/41; 606/48; 606/49; 606/50; 128/898
(58) Field of Classification Search .............. 607/96, 607/101, 102, 104, 105, 113, 116, 119, 115; 128/898; 606/41, 42, 45, 46, 48–50
See application file for complete search history.

(56) References Cited

U.S. PATENT DOCUMENTS

| 5,403,311 | A | * | 4/1995 | Abele et al. .................. 606/49 |
| 5,431,649 | A |   | 7/1995 | Mulier et al. |
| 6,016,809 | A | * | 1/2000 | Mulier et al. ............... 128/898 |
| 6,033,402 | A | * | 3/2000 | Tu et al. ....................... 606/41 |
| 6,866,650 | B2 | * | 3/2005 | Stevens et al. ........ 604/102.01 |

OTHER PUBLICATIONS

Gaiser, John, "Future Catheter Designs for Interventional Electrophysiology", Interventional Electrophysiology, Chapter 16, p. 469-532.
Hoey, Michael F., et al. "Intramural Ablation Using Radiofrequency Energy Via Screw-Tip Catheter and Saline Electrode", PACE, vol. 18, , Apr. 1995, Part II (Abstract).

\* cited by examiner

*Primary Examiner*—Rosiland Rollins
(74) *Attorney, Agent, or Firm*—Christie, Parker & Hale, LLP

(57) ABSTRACT

A method for ablating tissue in or around the heart to create an enhanced lesion is provided. The distal end of a catheter including a needle electrode at its distal end is introduced into the heart. The distal end of the needle electrode is introduced into the tissue. An electrically-conductive fluid is infused through the needle electrode and into the tissue. The tissue is ablated after and/or during introduction of the fluid into the tissue. The fluid conducts ablation energy within the tissue to create a larger lesion than would be created without the introduction of the fluid.

42 Claims, 15 Drawing Sheets

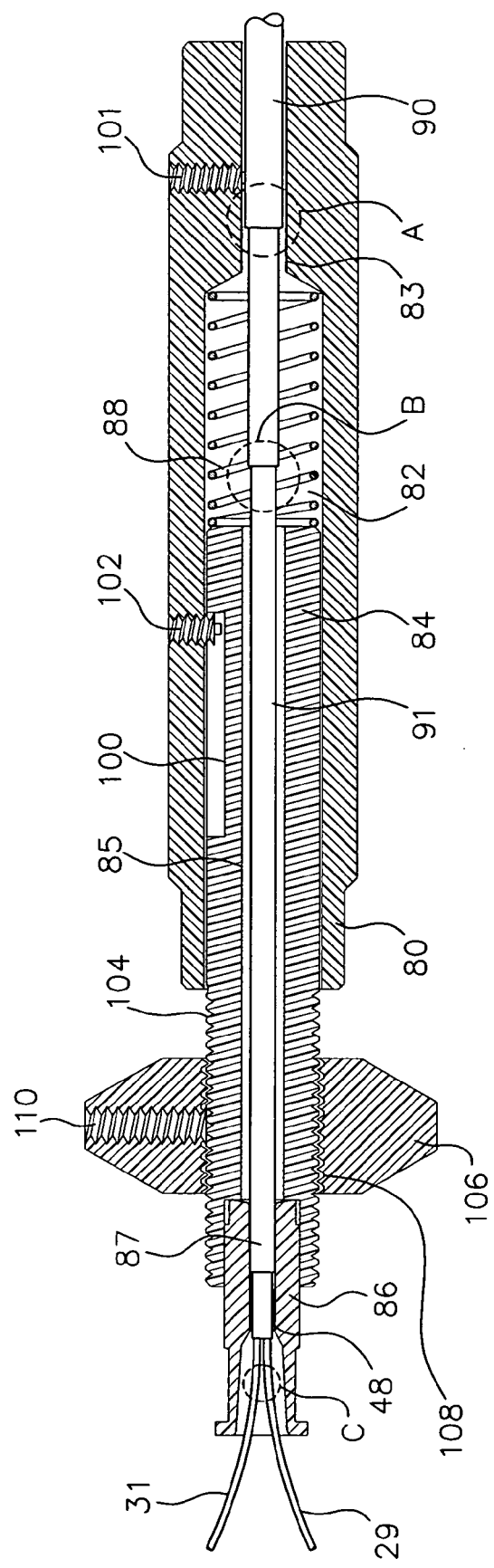

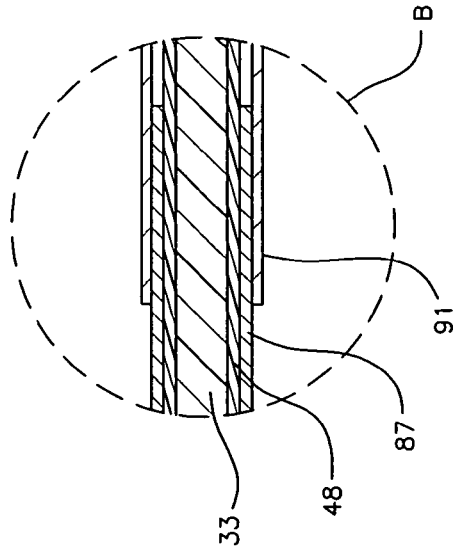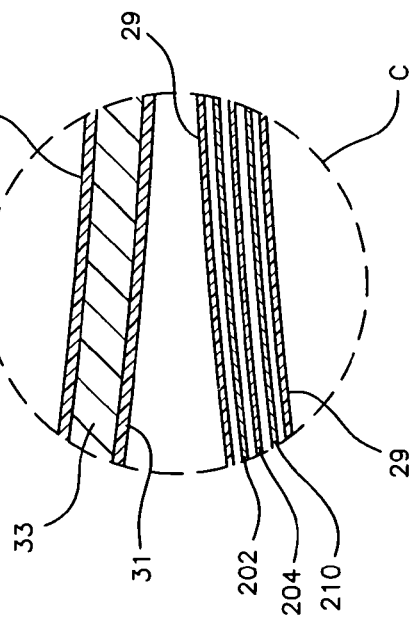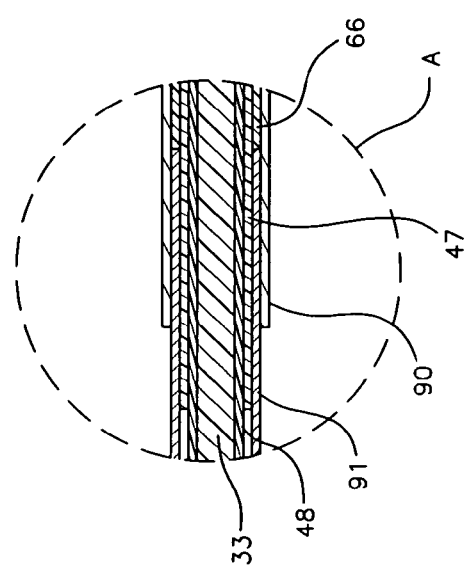

METHOD FOR ABLATING WITH NEEDLE ELECTRODE

FIELD OF THE INVENTION

This invention relates to methods for enhancing ablation by infusing a conductive fluid through a needle electrode.

BACKGROUND OF THE INVENTION

Radiofrequency (RF) ablation of cardiac and other tissue is a well known method for creating thermal injury lesions at the tip of an electrode. Radiofrequency current is delivered between a skin (ground) patch and the electrode. Electrical resistance at the electrode-tissue interface results in direct resistive heating of a small area, the size of which depends upon the size of the electrode, electrode tissue contact, and current (density). See Avitall B, Helms R. Determinants or Radiofrequency-Induced Lesion Size in Huang S K S, Wilber D J (eds.): Radiofrequency Catheter Ablation of Cardiac Arrhythmias: Basic Concepts and Clinical Applications, $2^{nd}$ ed. Armonk, N.Y., Futura Publishing Company, Inc., 2000: 47–80. Further tissue heating results from conduction of heat within the tissue to a larger zone. Tissue heated beyond a threshold of approximately 50–55° C. is irreversibly injured (ablated). See Nath S, and Haines D E. Pathophysiology of Lesion Formation by Radiofrequency Catheter Ablation, in Huang S K S, Wilber D J (eds.): Radiofrequency Catheter Ablation of Cardiac Arrhythmias: Basic Concepts and Clinical Applications, $2^{nd}$ ed. Armonk, N.Y., Futura Publishing Company, Inc., 2000: 26–28.

Resistive heating is caused by energy absorption due to electrical resistance. Energy absorption is related to the square of current density and inversely with tissue conductivity. Current density varies with conductivity and voltage and inversely with the square of radius from the ablating electrode. Therefore, energy absorption varies with conductivity, the square of applied voltage, and inversely with the fourth power of radius from the electrode. Resistive heating, therefore, is most heavily influenced by radius, and penetrates a very small distance from the ablating electrode. The rest of the lesion is created by thermal conduction from the area of resistive heating. See Lin J, Physical Aspects of Radiofrequency Ablation, in Huang S K S, Wilber D J (eds.): Radiofrequency Catheter Ablation of Cardiac Arrhythmias: Basic Concepts and Clinical Applications, $2^{nd}$ ed. Armonk, N.Y., Futura Publishing Company, Inc., 2000: 14–17. This imposes a limit on the size of ablation lesions that can be delivered from a surface electrode.

Theoretical methods to increase lesion size would include increasing electrode diameter, increasing the area of electrode contact with tissue, increasing tissue conductivity and penetrating the tissue to achieve greater depth and increase the area of contact, and delivering RF until maximal lesion size has been achieved (60–120 seconds for full maturation).

The electrode can be introduced to the tissue of interest directly (for superficial/skin structures), surgically, endoscopically, laparoscopically or using percutaneous transvascular (catheter-based) access. Catheter ablation is a well-described and commonly performed method by which many cardiac arrhythmias are treated. See Miller J M, Zipes D P. Management of the Patient with Cardiac Arrhythmias. In Braunwald E, Zipes D, Libby P (eds): Heart Disease: A Textbook of Cardiovascular Medicine, $6^{th}$ Ed. Philadelphia, Pa., W.B. Saunders Company, 2001: p742–752. Needle electrodes have been described for percutaneous or endoscopic ablation of solid-organ tumours, lung tumours, and abnormal neurologic structures. See, for example, McGahan J P, Schneider P, Brock J M, Tesluk H. Treatment of Liver Tumors by Percutaneous Radiofrequency Electrocautery. Seminars in Interventional Radiology 1993; 10: 143–149; Rossi S, Fornari F, Buscarini L. Percutaneous Ultrasound-Guided Radiofrequency Electrocautery for the Treatment of Small Hepatocellular Carcinoma. J Intervent Radiol 1993; 8: 97–103; and Livraghi T, Goldberg S N, Lazzaroni S, Meloni F, Monti F, Solbiati L. Saline-enhanced RF tissue ablation in the treatment of liver Metastases. Radiology 1995; 197(P): 140 (abstr)].

Catheter ablation is sometimes limited by insufficient lesion size. See de Bakker J M T, van Capelle F J L, Janse M J et al. Macroreentry in the infarcted human heart: mechanism of ventricular tacycardias with a "focal" activation pattern. J Am Coll Cardiol 1991; 18:1005–1014; Kaltenbrunner W, Cardinal R, Dubuc M et al. Epicardial and endocardial mapping of ventricular tachycardia in patients with myocardial infarction. Is the origin of the tachycardia always subendocardially localized? Circulation 1991; 84: 1058–1071. Stevenson W G, Friedman P L, Sager P T et al. Exploring postinfarction reentrant ventricular tachycardia with entrainment mapping. J Am coll Cardiol 1997; 29: 1180–1189. Ablation of tissue from an endovascular approach results not only in heating of tissue, but of heating of the electrode. When the electrode reaches critical temperatures, denaturation of blood proteins causes formation of a high resistance coagulum that limits current delivery. Within tissue, overheating can cause evaporation of tissue or blood water and steam bubble formation that can "explode" through the myocardial wall (steam "pops") with risk of uncontrolled tissue destruction or undesirable perforation of bodily structures. In cardiac ablation, clinical success is sometimes hampered by inadequate lesion depth and transverse diameter even when using catheters with active cooling of the tip. See Soejima K, Delacretaz E, Suzuki M et al. Saline-cooled versus standard radiofrequency catheter ablation for infarct-related ventricular tachycardias. Circulation 2001; 103:1858–1862. Theoretical solutions have included increasing the electrode size (increasing contact surface and increasing convective cooling by blood flow), improving electrode-tissue contact, actively cooling the electrode with fluid infusion, changing the material composition of the electrode to improve current delivery to tissue, and pulsing current delivery to allow intermittent cooling. Needle electrodes improve contact with tissue and allow deep penetration of current delivery to areas of interest. Ablation may still be hampered by the small surface area of the needle electrode such that heating occurs at low power, and small lesions are created. Accordingly, a need exists for a method for creating improved lesions.

SUMMARY OF THE INVENTION

The invention concerns a novel method for endovascular percutaneous ablation of mammalian tissue, including cardiac tissue. This invention is useful for destroying abnormal cardiac tissue such as myocardial reentry circuits causing arrhythmias, hypertrophic cardiomyopathy causing flow obstruction, or other tissues which may be approached endovascularly. A theoretic increase in the effective size of the electrode can be achieved by delivering conductive fluid through the needle. The fluid infiltrates the interstitium of the tissue of interest, and conducts current rapidly over a greater volume of tissue, creating a larger area of resistive heating, with a significantly larger surface area, and a consequently significantly larger volume of tissue heated by conductive heating.

In one embodiment, the invention is directed to a method for ablating tissue in or around the heart to create an enhanced lesion. The distal end of a catheter including a needle electrode at its distal end is introduced into the heart. The distal end of the needle electrode is introduced into the tissue. An electrically-conductive fluid is infused through the needle electrode and into the tissue. The tissue is ablated after and/or during introduction of the fluid into the tissue. The fluid conducts ablation energy within the tissue to create a larger lesion than would be created without the introduction of the fluid.

DESCRIPTION OF THE DRAWINGS

These and other features and advantages of the present invention will be better understood by reference to the following detailed description when considered in conjunction with the accompanying drawings wherein:

FIG. 8 is a side cross-sectional view of the needle control handle where the needle is in a retracted position;

DETAILED DESCRIPTION

Figure 1:
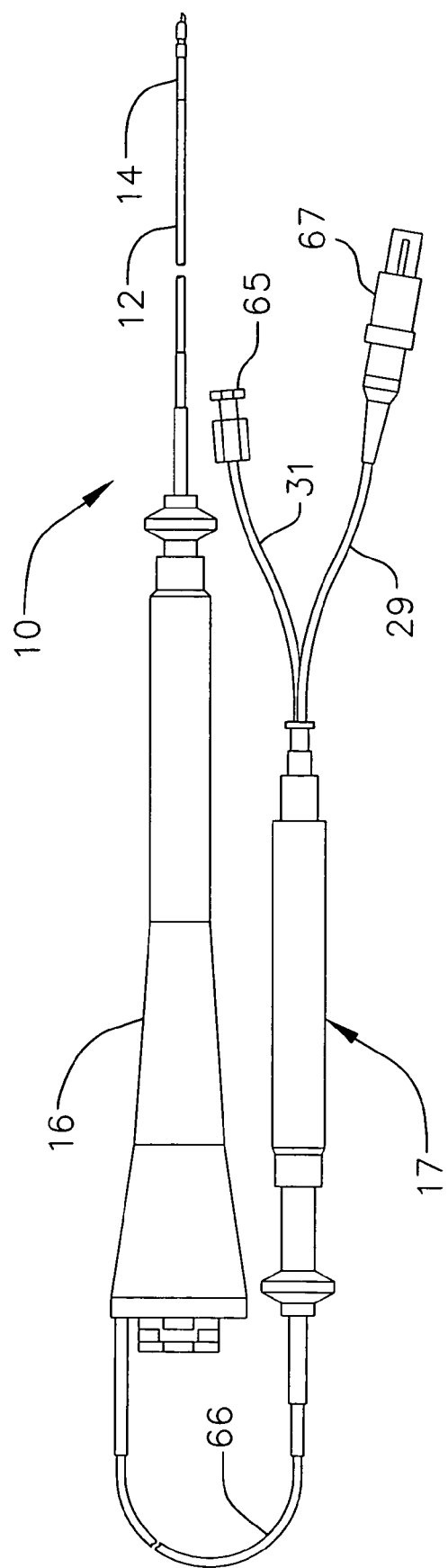
FIG. 1 is a side plan view of a catheter according to the present invention.

In one embodiment of the invention, there is provided a catheter particularly useful for ablating tissue in the heart. As shown in FIG. 1, the catheter comprises an elongated proximal shaft 10 having a proximal shaft 12 and a distal shaft 14. A deflection control handle 16 is mounted at the proximal end of the proximal shaft 12, and a needle control handle 17 is attached indirectly to the proximal shaft proximal to the deflection control handle.

Figure 2:
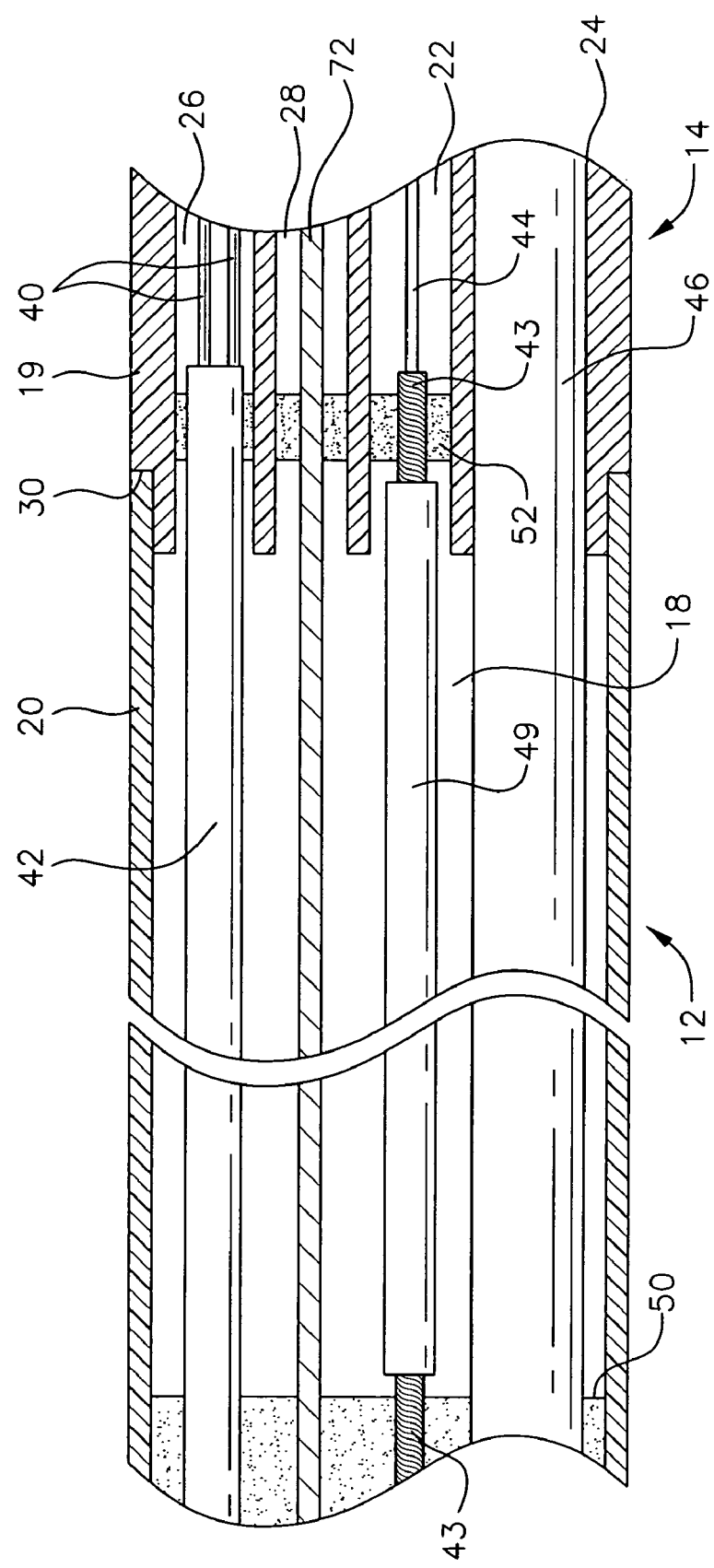
FIG. 2 is a side cross-sectional view of the proximal shaft, including the junction between the proximal shaft and the distal shaft.

With reference to FIG. 2, the proximal shaft 12 comprises a single, central or axial lumen 18. The proximal shaft 12 is flexible, i.e., bendable, but substantially non-compressible along its length. The proximal shaft 12 may be of any suitable construction and made of any suitable material. A presently preferred construction comprises an outer wall 20 made of a polyurethane or nylon. The outer wall 20 comprises an imbedded braided mesh (not shown) of stainless steel or the like to increase torsional stiffness of the proximal shaft 12 so that, when the deflection control handle 16 is rotated, the distal shaft 14 will rotate in a corresponding manner. The outer diameter of the proximal shaft 12 is not critical, but is preferably no more than about 8 French. Likewise the thickness of the outer wall 20 is not critical.

Figure 3:
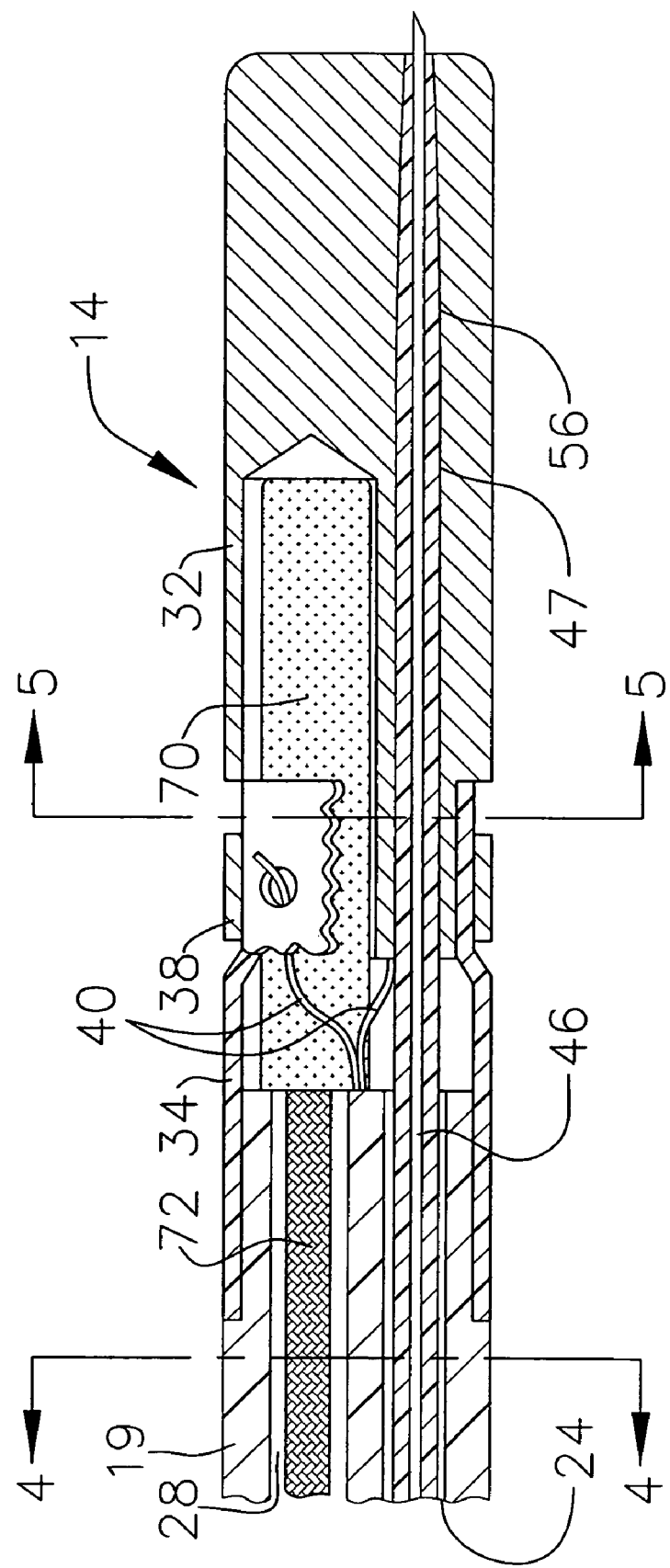
FIG. 3 is a side cross-sectional view of the distal shaft showing the arrangement of the electromagnetic mapping sensor, needle electrode and tip electrode.
Figure 4:
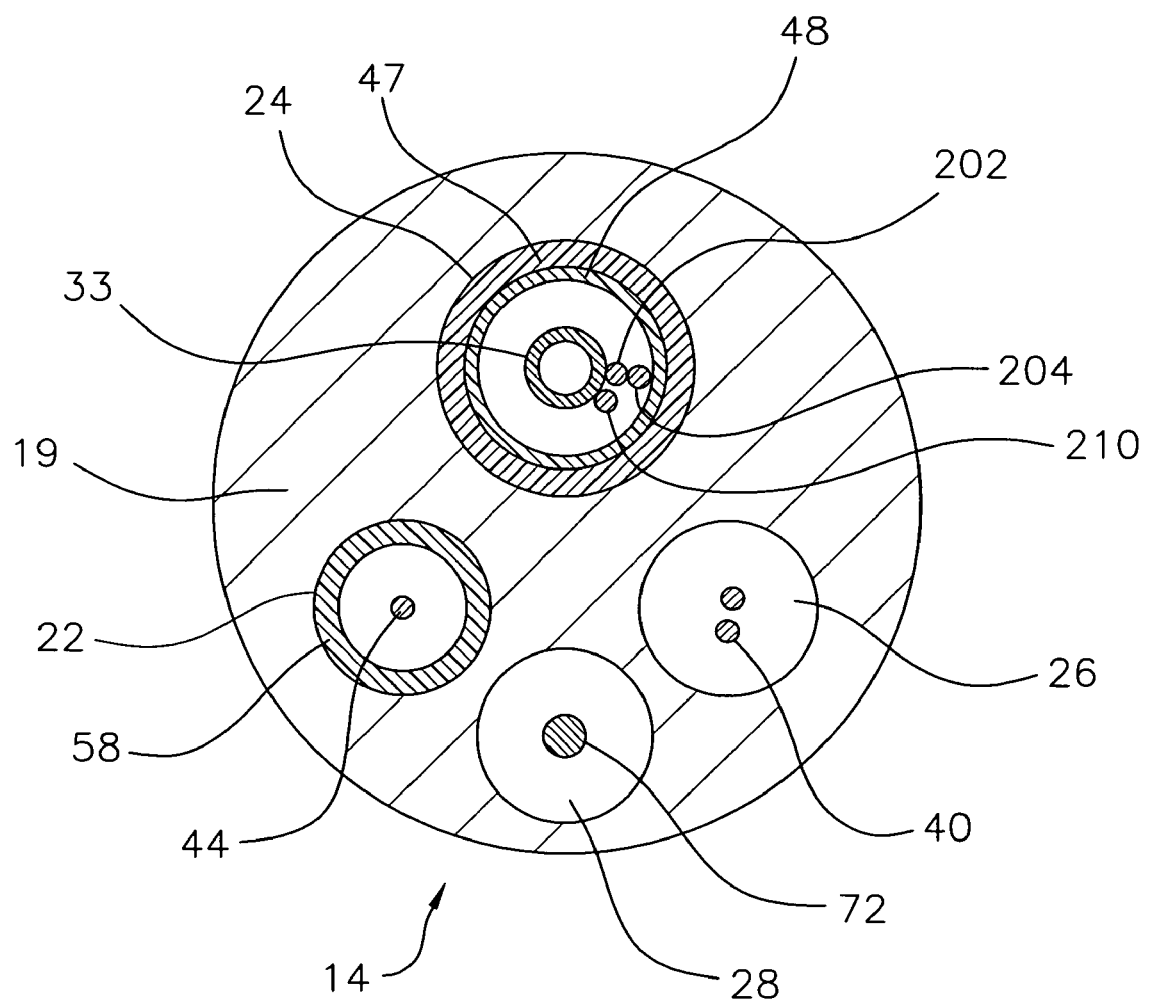
FIG. 4 is an end cross-sectional view of the distal shaft shown in FIG. 3 along line 4—4.

As shown in FIGS. 2 to 4, the distal shaft 14 comprises a short section of tubing 19 having four lumens, namely, a puller wire lumen 22, an infusion lumen 24, a lead wire lumen 26 and a sensor cable lumen 28. The tubing 19 is made of a suitable non-toxic material which is preferably more flexible than the proximal shaft 12. A presently preferred material for the tubing 19 is braided polyurethane, i.e., polyurethane with an embedded mesh of braided stainless steel or the like. The outer diameter of the distal shaft 14, like that of the proximal shaft 12, is preferably no greater than about 8 French. The size of the lumens is not critical. In a particularly preferred embodiment, the distal shaft 14 has an outer diameter of about 0.096 inch, the infusion lumen 24 has a diameter of about 0.044 inch, and the puller wire lumen 22, lead wire lumen 26 and sensor cable lumen 28 each have a diameter of about 0.022 inch.

A preferred means for attaching the proximal shaft 12 to the distal shaft 14 is illustrated in FIG. 2. The proximal end of the distal shaft 14 comprises an outer circumferential notch 30 that receives the inner surface of the outer wall 20 of the proximal shaft 12. The distal shaft 14 and proximal shaft 12 are attached by glue or the like.

Figure 5:
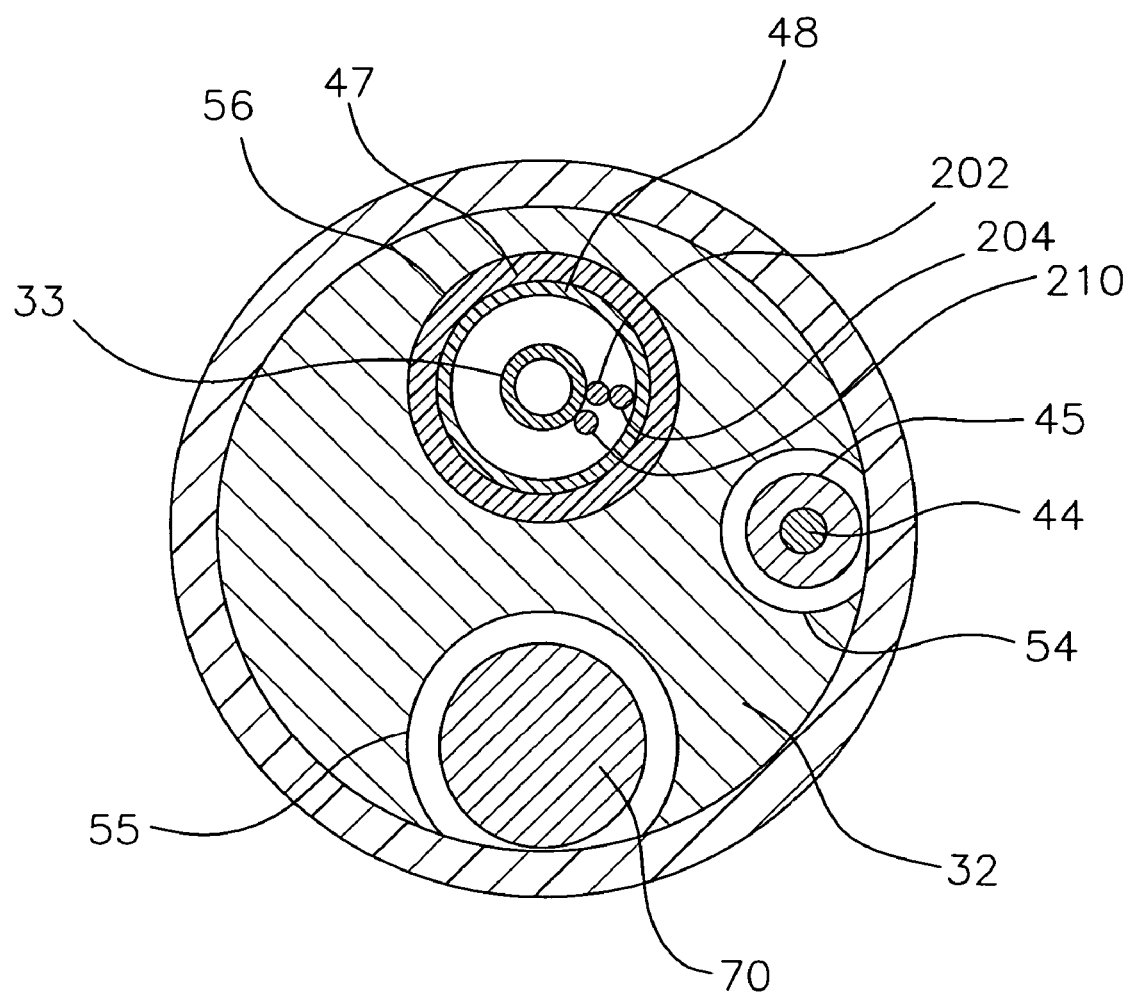
FIG. 5 is an end cross-sectional view of the tip electrode shown in FIG. 3 along line 5—5.

With reference to FIGS. 3 and 5, mounted at the distal end of the distal shaft 14 is a tip electrode 32. For clarity, FIG. 3 only shows two of the four lumens of the distal shaft 14. Preferably the tip electrode 32 has a diameter about the same as the outer diameter of the tubing 19. The tip electrode 32 is connected to the tubing 19 by a plastic housing 34, preferably made of polyetheretherketone (PEEK). The proximal end of the tip electrode 32 is notched circumferentially and fits inside the distal end of the plastic housing 34 and is bonded to the housing by polyurethane glue or the like. The proximal end of the plastic housing 34 is bonded with polyurethane glue or the like to the distal end of the tubing 19 of the distal shaft 14. Alternatively, the tip electrode 32 can be mounted directly to the distal end of the flexible tubing 19 of the distal shaft 14.

Mounted on the distal end of the plastic housing 34 is a ring electrode 38. The ring electrode 38 is slid over the plastic housing 34 and fixed in place by glue or the like. If desired, additional ring electrodes may be used and can be positioned over the plastic housing 34 and/or over the flexible tubing 19 of the distal shaft 14.

The tip electrode 32 and ring electrode 38 are each connected to a separate electrode lead wire 40. The electrode lead wires 40, which each include an insulating coating, extend through the lead wire lumen 26 of distal shaft 14, the proximal shaft 12, and the deflection control handle 16, and terminate at their proximal end in an input jack (not shown) that may be plugged into an appropriate monitor (not shown). In the depicted embodiment, the portion of the electrode lead wires 40 extending through the proximal shaft 12 and deflection control handle 16 are enclosed within a protective sheath 42.

The electrode lead wires 40 are attached to the tip electrode 32 and ring electrode 38 by any conventional technique. Connection of an electrode lead wire 40 to the tip electrode 32 or ring electrode 38 is preferably accomplished by welding the electrode lead wire's distal end, which is stripped of its insulative coating, to the corresponding tip electrode or ring electrode.

A puller wire 44 is provided for deflection of the distal shaft 14. The puller wire 44 is anchored at its proximal end to the deflection control handle 16 and anchored at its distal end to the distal shaft 14, which. The puller wire 44 is made of any suitable metal, such as stainless steel or Nitinol, and is preferably coated with Teflon® or the like. The coating imparts lubricity to the puller wire 44. The puller wire 44 preferably has a diameter ranging from about 0.006 to about 0.010 inches.

A compression coil 43 extends from the proximal end of the proximal shaft 12 to the proximal end of the distal shaft 14. The compression coil 43 is made of any suitable metal, preferably stainless steel. The compression coil 43 is tightly wound on itself to provide flexibility, i.e., bending, but to resist compression. The inner diameter of the compression coil 43 is preferably slightly larger than the diameter of the puller wire 44. For example, when the puller wire 44 has a diameter of about 0.007 inches, the compression coil 43 preferably has an inner diameter of about 0.008 inches. The Teflon® coating on the puller wire 44 allows it to slide freely within the compression coil 43. Along its length, the outer surface of the compression coil 43 is covered by a flexible, non-conductive sheath 49 to prevent contact between the compression coil 43 and any of the other components within the proximal shaft 12. A non-conductive sheath 49 made of polyimide tubing is presently preferred. As shown in FIG. 2, the compression coil 43 is anchored at its proximal end to the proximal end of the proximal shaft 12 by glue to form a glue joint 50 and at its distal end to the distal shaft 14 in the puller wire lumen 22 by glue to form a glue joint 52, but other arrangements are contemplated within the invention.

The puller wire 44 extends into the puller wire lumen 22 of the distal shaft 14. In the depicted embodiment, the puller wire 44 is anchored in a first blind hole 54 of the tip electrode 32. Preferably, a ferrule 41, made of stainless steel or the like, is crimped onto the distal end of the puller wire 44 to add thickness to the puller wire. The ferrule 41 is then attached to the inside of the first blind hole 54 of the tip electrode 32 with solder or the like. Alternatively, the puller wire 44 can be anchored to the sidewall of the distal shaft 14. Within the distal shaft 14, the puller wire 44 extends through into a plastic, preferably Teflon®, sheath 58, which prevents the puller wire 44 from cutting into the wall of the distal shaft when the distal shaft is deflected.

Longitudinal movement of the puller wire 44 relative to the proximal shaft 12, which results in deflection of the distal shaft 14, is accomplished by suitable manipulation of the deflection control handle 16. Examples of suitable control handles for use in the present invention are disclosed, for example, in U.S. Pat. Nos. Re 34,502, 5,897,529 and 6,575,931, the entire disclosures of which are incorporated herein by reference. Other control handles capable of affecting longitudinal movement of the puller wire relative to the catheter body can be used in the invention.

If desired, the catheter can include two or more puller wires (not shown) to enhance the ability to manipulate the distal shaft 14. In such an embodiment, a second puller wire and a surrounding second compression coil extend through the proximal shaft 12 and into separate off-axis lumens (not shown) in the distal shaft. Suitable deflection control handles for use with a catheter having more than one puller wire are described in U.S. Pat. Nos. 6,123,699, 6,171,277, and 6,183,463, the disclosures of which are incorporated herein by reference.

Figure 6:
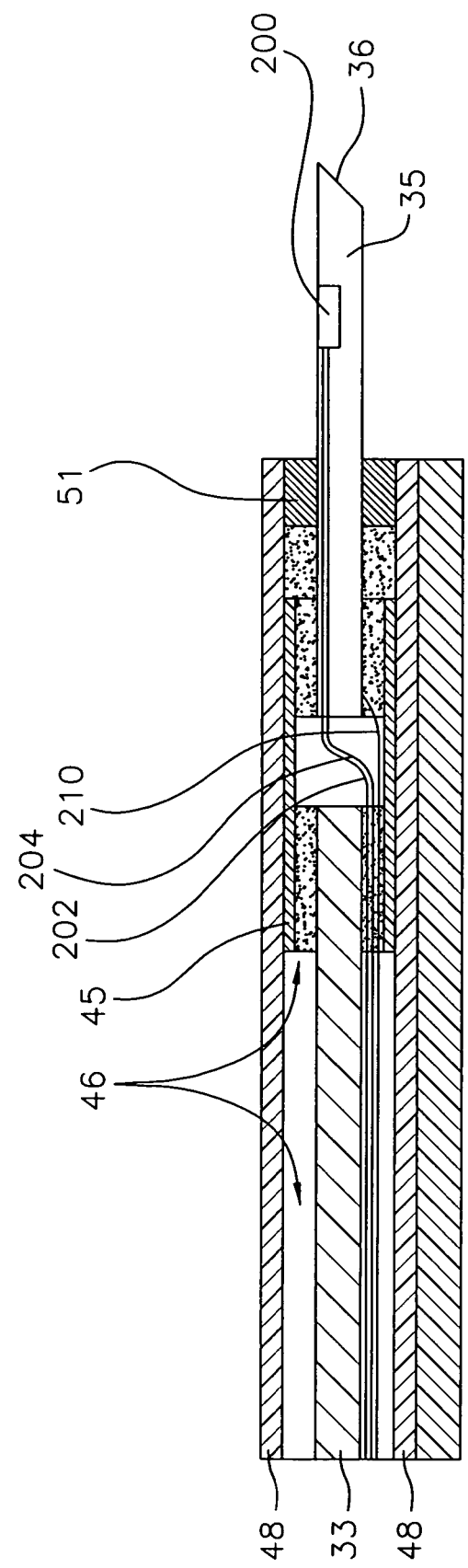
FIG. 6 is an enlarged view of the needle electrode assembly shown in FIG. 3.

As shown in FIGS. 3 and 6, a needle electrode assembly 46 is provided within the catheter. The needle electrode assembly 46 is used to ablate tissue while simultaneously injecting saline or other fluid to conduct the ablation energy, thereby creating a theoretic increase in the effective size of the electrode. The needle electrode assembly 46 is extendable and retractable, and may be moved by manipulation of the needle control handle 17, as described further below. FIG. 3 depicts the needle electrode assembly 46 in an extended position as it would be to ablate tissue. The distal end of the needle electrode assembly 46 may be withdrawn into the catheter to avoid injury, particularly during the time that the catheter is inserted through the vasculature of the body and during the time in which the catheter is removed from the body.

The needle electrode assembly 46 comprises a proximal tubing 33 joined, directly or indirectly, to a generally rigid, electrically-conductive distal tubing 35, as shown in FIG. 3. The generally rigid nature of the distal tubing 35 allows it to pierce tissue in order to increase its effectiveness during ablation. For example, the distal tubing 35 can be formed of Nitinol (or other nickel-titanium alloy), gold, platinum, stainless steel, or an alloy thereof, and, as illustrated in FIG. 3, is preferably formed with a beveled edge 36 at the distal tip of the needle electrode assembly 46 to enhance its ability to pierce tissue. The diameter distal tubing 35 can vary, for example, from about 18 gauge to about 29 gauge, and more particularly can be about 27 gauge. If desired, the distal tubing 35 can include one or more irrigation ports in its sidewall in addition to or instead of the opening at the distal end of the distal tubing. Such a design is described in U.S. Pat. No. 6,575,931, the disclosure of which is incorporated herein by reference.

The proximal tubing 33 is preferably more flexible than the distal tubing 35 to allow the proximal tubing to bend as necessary with the flexible proximal shaft 13 of the catheter body 12, for instance when the catheter is inserted into the vasculature of the body. The proximal tubing 33 of the needle electrode assembly 46 is preferably made of polyimide or polyether etherketone (PEEK), but can be made of any other suitable biocompatible material, such as plastic or metal.

A needle electrode lead wire 210 is electrically connected at its distal end to the electrically-conductive distal tubing 35 for supplying radio frequency energy or other suitable ablation energy to the distal tubing. The needle electrode lead wire 210 is soldered, welded or otherwise attached to the outside of the distal tubing 35, but could be attached elsewhere to the distal tubing. The proximal end of the needle electrode lead wire 210 is attached to a suitable connector 67, which in turn is connected to a suitable source of ablation energy (not shown).

Figure 7:
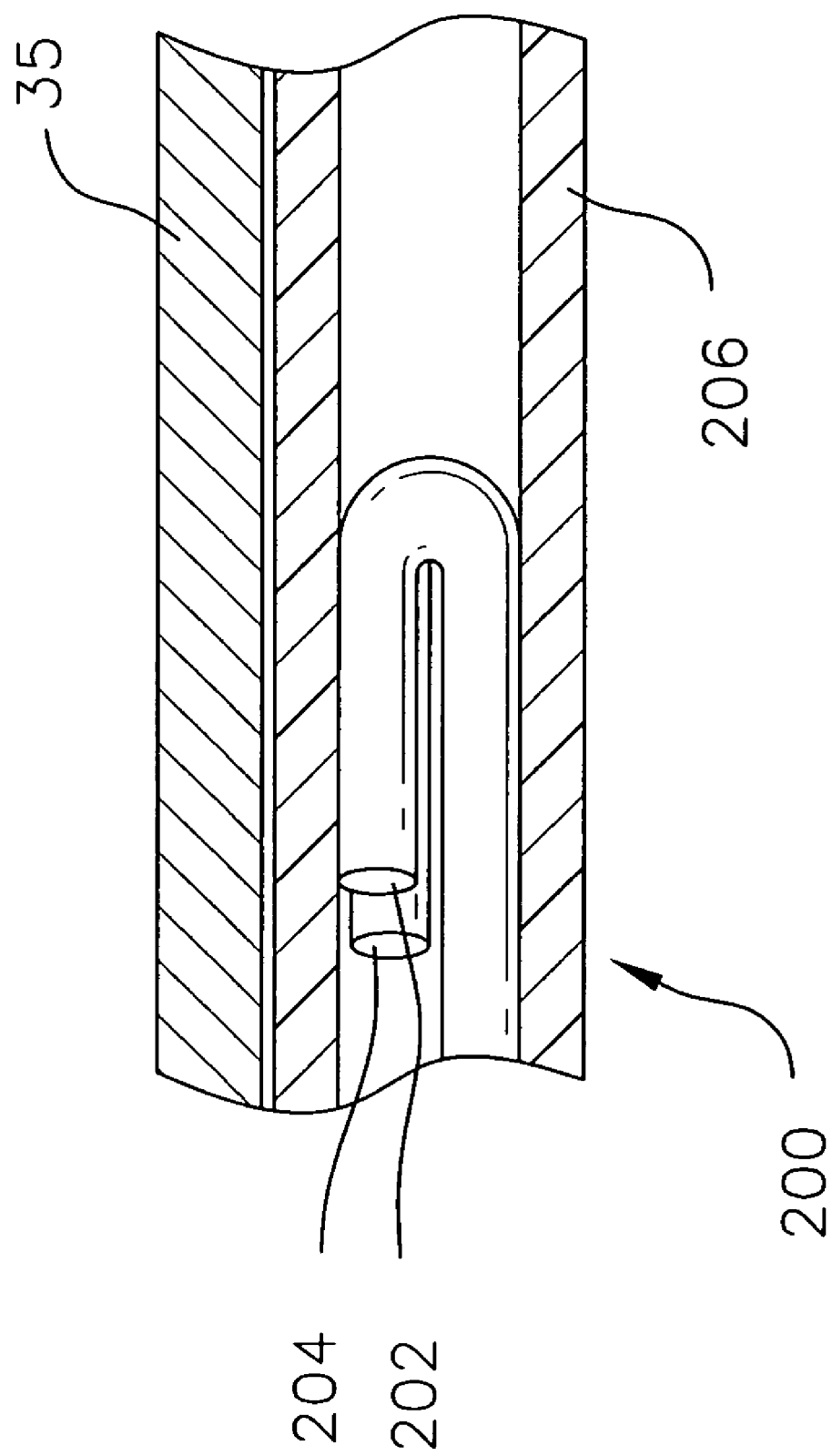
FIG. 7 is an enlarged side cross-sectional view of the thermocouple mounted in the needle electrode assembly shown in FIG. 3.

Additionally, a temperature sensor is provided for measuring the temperature of the tissue being ablated by the needle electrode assembly 46 before, during or after ablation. Any conventional temperature sensor, e.g., a thermocouple or thermistor, may be used. In the depicted embodiment, the temperature sensor comprises a thermocouple 200 formed by an enameled wire pair. One wire of the wire pair is a copper wire 202, e.g., a number 40 copper wire. The other wire of the wire pair is a constantan wire 204. The wires 202 and 204 of the wire pair are electrically isolated from each other except at their distal ends, where they are twisted together, covered with a short piece of plastic tubing 206, e.g., polyimide, and covered with epoxy, as shown in FIG. 7. The plastic tubing 206 is then glued or otherwise attached to the inside wall of the distal tubing 35 of the needle electrode assembly 46. The proximal ends of the wires 202 and 204 extend out the proximal end of the distal tubing 35 and are attached to an appropriate connector 67 connectable to a suitable temperature monitor (not shown), as described in more detail below. In an alternative embodiment, the copper wire 202 of the thermocouple can also be used as the lead wire for the needle electrode assembly 46. The temperature sensor can be eliminated if desired or can be mounted in any other part of the needle assembly 46, distal shaft 14 and/or tip electrode 32.

The proximal tubing 33 of the needle electrode assembly 46 extends from the needle control handle 17, through the deflection control handle 16, through the proximal shaft 13, and into the infusion lumen 24 of the distal shaft 14. The proximal end of the distal tubing 35 is spaced slightly from the distal end of the proximal tubing 33 and extends through the infusion lumen 30 of the distal shaft 14. The proximal and distal tubings 33 and 35 are mounted, preferably coaxially, within an outer plastic tube 48. The outer plastic tube 48 can be glued or otherwise attached to the proximal and distal tubings to form a single structure that, as described below, is longitudinally moveable relative to the catheter body 12. The outer plastic tube 48 extends through the catheter body 12 with the proximal tubing and protects the needle electrode lead wire 210 and thermocouple wires 202 and 204, which extend between the proximal tubing 33 and outer plastic tube 48, when the needle electrode assembly 46 is moved relative to the distal shaft 14. The needle electrode lead wire 210 and thermocouple wires 202 and 204 extend out through a hole (not shown) in the outer plastic tube 48 within the deflection control handle 16 and are attached to appropriate connectors, as noted above.

FIG. 6 shows one arrangement for joining the outer plastic tube 48 to the proximal and distal tubings 33 and 35. Specifically, a small piece of plastic tubing 45, for example, polyimide tubing, is placed over the discontinuity between the proximal and distal tubings 33 and 35 and attached to the proximal and distal tubings by polyurethane glue or the like to form a single infusion passage through which saline or other fluid can pass from the proximal tubing to the distal tubing. The small piece of plastic tubing 45 helps to protect the thermocouple wires 202 and 204 and the needle electrode lead wire 210. A small, preferably non-conductive, spacer 51 is mounted between the distal tubing 35 and the distal end of the outer plastic tube 48, and optionally glued in place. The spacer 51 prevents bodily fluid from entering into the distal end of the needle electrode assembly 46. In FIG. 6, the relative sizes and positions of the tubings 33, 35, 45 and 48 are exaggerated for clarity.

In an exemplary embodiment, the proximal tubing 33 of the needle electrode assembly 46 has an inner diameter of 0.014 inch and an outer diameter of 0.016 inch. The distal tubing 35 has an inner diameter of 0.014 inch and an outer diameter of 0.018 inch and a length of about 1.0 inch. Further, the distal tubing 35 extends past the distal end of the distal shaft 14 about 14 mm. The small plastic tubing 45 has an inner diameter of 0.022 inch and an outer diameter of 0.024, the outer plastic tube 48 has an inner diameter of 0.025 inch and an outer diameter of 0.035 inch, and the plastic spacer 51 has an inner diameter of 0.017 inch and an outer diameter of 0.024 inch.

Within the proximal shaft 12 and distal shaft 14, the needle electrode assembly 46, comprising the proximal tubing 33, distal tubing 35, spacer 51, plastic tubing 45 and outer plastic tube 48, is slidably mounted, preferably coaxially, within a protective tube 47 that is stationary relative to the catheter body. The protective tube 47 has a distal end glued into a passage 56 that extends through the tip electrode 32. The protective tube 47, which is preferably made of polyimide, serves to prevent the needle electrode assembly 46 from buckling during extension and retraction of the needle electrode assembly relative to the catheter body 12. The protective tube 47 additionally serves to provide a fluid-tight seal surrounding the needle electrode assembly 46. Within the deflection control handle 16, the protective tube 47 and needle electrode assembly 46 extend into a protective shaft 66, which is preferably made of polyurethane.

Other needle electrode assembly designs are contemplated within the scope of the invention. For example, the needle electrode assembly can comprise a single electrically-conductive tube, such as a Nitinol tube, that extends from the needle control handle 17 to the distal end of the catheter. Such a design is described in U.S. patent application Ser. No. 09/711,648, entitled "Injection Catheter with Needle Electrode," the disclosure of which is incorporated herein by reference.

Longitudinal movement of the needle electrode assembly 46 is achieved using the needle control handle 17. The needle electrode assembly 46 and protective tube 47 extend from the deflection control handle 16 to the needle control handle 17 within the protective shaft 66.

As illustrated in FIG. 8, in one embodiment the needle control handle 17 comprises a generally cylindrical outer body 80 having proximal and distal ends, a piston chamber 82 extending a part of the way therethrough, and a needle passage 83 extending a part of the way therethrough. The piston chamber 82 extends from the proximal end of the handle part way into the body 80, but does not extend out the distal end of the body. The needle passage 83, which has a diameter less than that of the piston chamber 82, extends from the distal end of the piston chamber to the distal end of the outer body 80.

A piston 84, having proximal and distal ends, is slidably mounted within the piston chamber 82. A proximal fitting 86 is mounted in and fixedly attached to the proximal end of the piston 84. The proximal fitting 86 includes a tubular distal region 87 that extends distally from the main body of the proximal fitting. The piston 84 has an axial passage 85 through which the proximal tubing 33 of the needle electrode assembly 46 extends, as described in more detail below. A compression spring 88 is mounted within the piston chamber 82 between the distal end of the piston 84 and the outer body 80. The compression spring 88 can either be arranged between the piston 84 and outer body 80, or can have one end in contact with or fixed to the piston, while the other end is in contact with or fixed to the outer body.

The proximal tubing 33, outer plastic tube 48, protective tube 47 and protective shaft 66 extend from the deflection control handle 16 into the distal end of the needle passage 83, as best shown in AREA A of FIG. 8. Within the needle passage 83, the proximal tubing 33, outer plastic tube 48, protective tube 47 and protective shaft 66 extend into a first metal tube 90, which is preferably made of stainless steel. If desired, the first metal tube 90 could instead be made of a rigid plastic material. The first metal tube 90 is secured to the outer body 80 of the needle control handle 17 by a set screw 101 or any other suitable means. The protective shaft 66 terminates at its proximal end within the first metal tube 90.

A second metal tube 91 is provided with its distal end mounted, preferably coaxially, inside the proximal end of the first metal tube 90 and with its distal end abutting the proximal end of the protective shaft 66. The second metal tube 91 is fixed in place relative to the first metal tube 90 by the set screw 101. The second metal tube 91, like the first metal tube 90, could alternatively be made of a rigid plastic material.

The proximal end of the second metal tube 91 is mounted, preferably coaxially, around the distal end of the tubular distal region 87 of the proximal fitting 86, with the second metal tube being longitudinally movable relative to the tubular distal region 87. Accordingly, when the piston 84 is moved distally relative to the outer body 80, the tubular distal region 87 moves distally into the second metal tube 91. As shown in AREA B of FIG. 8, the proximal tubing 33 and outer plastic tube 48 extend through the second metal tube 91 and into the tubular distal region 87 of the proximal fitting 86. The outer plastic tube 48 terminates in and is fixedly attached to the proximal fitting 86 to thereby attach the outer plastic tube, and thus the needle electrode assembly 46, to the piston 84. Within the proximal fitting 86, the proximal tubing 33 extends out of the outer plastic tube 48 and into a first protective sheath 31, as shown in AREA C of FIG. 8, and is connected to a luer connector 65, which is connected to an irrigation pump or other suitable fluid infusion source (not shown), as is known in the art. Similarly, the needle electrode lead wire 210 and the thermocouple wires 202 and 204 extend out of the outer plastic tube 48 and into a second protective sheath 29, as also shown in AREA C of FIG. 2, which is connected to a suitable connector 67, such as a 10-pin electrical connector, for connecting the needle electrode lead wire to a source of ablation energy and the thermocouple wires to a suitable monitoring system.

In use, force is applied to the piston 84 to cause distal movement of the piston relative to the outer body 80, which compresses the compression spring 88. This movement causes the needle electrode assembly 46 to correspondingly move distally relative to the outer body 80, protective shaft 66, protective tube 47, proximal shaft 13, and distal shaft 14 so that the distal tubing 35 of the needle electrode assembly extends outside the distal end of the distal shaft. When the force is removed from the piston 84, the compression spring 88 pushes the piston proximally to its original position, thus causing the distal tubing 35 of the needle electrode assembly 46 to retract back into the distal end of the distal shaft 14. Upon distal movement of the piston 84, the tubular distal region 87 of the proximal fitting 86 moves distally into the second metal tube 91 to prevent the proximal tubing 33 and the outer plastic tube 48 of the needle electrode assembly 46 from buckling within the axial passage 85.

The piston 84 further comprises a longitudinal slot 100 extending along a portion of its outer edge. A securing means 102, such as a set screw, pin, or other locking mechanism, extends through the outer body 80 and into the longitudinal slot 100. This design limits the distance that the piston 84 can be slid proximally out of the piston chamber 82. When the needle electrode assembly 46 is in the retracted position, preferably the securing means 102 is at or near the distal end of the longitudinal slot 100.

The proximal end of the piston 84 has a threaded outer surface 104. A circular thumb control 106 is rotatably mounted on the proximal end of the piston 84. The thumb control 106 has a threaded inner surface 108 that interacts with the threaded outer surface 104 of the piston. The thumb control 106 acts as a stop, limiting the distance that the piston 84 can be pushed into the piston chamber 82, and thus the distance that the needle electrode assembly 46 can be extended out of the distal end of the catheter. The threaded surfaces of the thumb control 106 and piston 84 allow the thumb control to be moved closer or farther from the proximal end of the outer body 80 so that the extension distance of the needle electrode assembly 46 can be controlled by the physician. A securing means, such as a tension screw 110 is provided in the thumb control 106 to control the tension between the thumb control and piston 84. As would be recognized by one skilled in the art, the thumb control 106 can be replaced by any other mechanism that can act as a stop for limiting the distance that the piston 84 extends into the piston chamber 82, and it is not necessary, although it is preferred, that the stop be adjustable relative to the piston.

Additionally, a location sensor 70 is contained within the distal end of the distal shaft 14. The location sensor 70 is used to determine the coordinates of the distal end of the catheter, for example, during mapping of electrical activity or during placement of the distal end of the catheter for ablation. In the depicted embodiment, a single location sensor 70 is mounted in the distal end of the distal shaft 14, partly within a second blind hole 55 in the tip electrode 32 and partly within the plastic housing 34.

The location sensor 70 is connected to a corresponding sensor cable 72. The sensor cable 72 extends through proximal shaft 12 and deflection control handle 16 and out of the proximal end of the deflection control handle within an umbilical cord (not shown) to a sensor control module (not shown) that houses a circuit board (not shown). Alternatively, the circuit board can be housed within the deflection control handle 16, for example, as described in U.S. Pat. No. 6,024,739, the disclosure of which is incorporated herein by reference. The sensor cable 72 comprises multiple wires encased within a plastic covered sheath. In the sensor control module, the wires of the sensor cable 72 are connected to the circuit board. The circuit board amplifies the signal received from the location sensor 70 and transmits it to a computer in a form understandable by the computer by means of a sensor connector at the proximal end of the sensor control module. Also, because the catheter is designed for single use only, the circuit board preferably contains an EPROM chip that shuts down the circuit board approximately twenty-four hours after the catheter has been used. This prevents the catheter, or at least the location sensor 70, from being used twice.

Preferably the location sensor 70 is an electromagnetic location sensor. For example, the location sensor 70 may comprise a magnetic-field-responsive coil, as described in U.S. Pat. No. 5,391,199, or a plurality of such coils, as described in International Publication WO 96/05758. The plurality of coils enables the six-dimensional coordinates (i.e. the three positional and the three orientational coordinates) of the location sensor 70 to be determined. Alternatively, any suitable location sensor known in the art may be used, such as electrical, magnetic or acoustic sensors. Suitable location sensors for use with the present invention are also described, for example, in U.S. Pat. Nos. 5,558,091, 5,443,489, 5,480,422, 5,546,951, and 5,568,809, International Publication Nos. WO 95/02995, WO 97/24983, and WO 98/29033, and U.S. patent application Ser. No. 09/882, 125 filed Jun. 15, 2001, entitled "Position Sensor Having Core with High Permeability Material," the disclosures of which are incorporated herein by reference. Using this technology, the physician can visually map a heart chamber. This mapping is done by advancing the distal shaft 14 into a heart chamber until contact is made with the heart wall. This position is recorded and saved. The distal shaft 14 is then moved to another position in contact with the heart wall and again the position is recorded and saved.

The electromagnetic mapping sensor 70 can be used alone or, more preferably, in combination with the tip electrode 32 and/or ring electrode 38. By combining the electromagnetic sensor 70 and electrodes 32 and 38, a physician can simultaneously map the contours or shape of the heart chamber, the electrical activity of the heart, and the extent of displacement of the catheter.

It is understood that, while it is preferred to include both electrophysiology electrodes (such as the tip electrode 32 and ring electrode 38) and an electromagnetic sensor in the distal shaft 14, it is not necessary to include both. For example, an ablation catheter having an electromagnetic sensor but no electrophysiology electrodes may be used in combination with a separate mapping catheter system. A preferred mapping system includes a catheter comprising multiple electrodes and an electromagnetic sensor, such as the NOGA-STAR catheter marketed by Biosense Webster, Inc., and means for monitoring and displaying the signals received from the electrodes and electromagnetic sensor, such as the Biosense-NOGA system, also marketed by Biosense Webster, Inc.

The catheters in accordance with the present invention are particularly suitable for ablating large, deep lesions in heart tissue. In operation, the distal end of the catheter is inserted into a vein or artery and advanced into the heart. To assist in positioning the distal shaft 14 of the catheter at a desired position within the heart, the puller wire 50 and deflection control handle 16 are used to deflect the distal shaft 14. Once the distal shaft 14 has been positioned at or near the desired location of the heart tissue, and preferably arranged generally perpendicular to the heart tissue, the distal end of the needle electrode assembly 46 is advanced distally, using the needle control handle 17, out of the distal end of the catheter and into the adjacent heart tissue.

The depth to which the distal end of the needle electrode assembly 46 is advanced into the heart tissue can vary depending on the desired size of the lesion to be produced. For example, the depth of the needle penetration can range from about 2 to about 30 mm, more particularly from about 3 to about 20 mm, still more particularly from about 4 to about 10 mm, even more particularly from about 5 to about 7 mm. The deeper the needle is advanced, the more needle surface area that is provided for ablation, but the greater the risk of perforation. The needle is preferably advanced a sufficient distance so that fluid infused through the needle goes into the heart tissue.

Fluid is then infused through the needle ablation assembly 46, before and/or during ablation, to enhance the ablation by serving as a virtual electrode. The fluid used should be biologically acceptable and should be able to conduct ablation energy from the needle electrode to the heart tissue. Preferably the fluid used is saline having a salt content ranging from about 0.3 to about 4 wt %, more particularly from about 0.5 to about 3 wt %, still more particularly from about 0.9 to about 2.5 wt %, even more particularly from about 0.9 to about 1.5 or 2 wt %.

If desired, the saline or other fluid being infused through can include a radiographic contrast agent, preferably comprising an iodinated compound, such as an iodinated contrast with diatrizoate salt with meglumine and sodium or an ioxaglate salt with meglumine and sodium; or a nonionic contrast with iohexol, iopamidol, iopromide, and/or ioversol. If used, the amount of contrast media present in the fluid can vary as desired, and can range, for example, from about 5 to about 50%, more particularly from about 10 to about 30%, still more particularly from about 10 to about 20%. The contrast agent permits the electrophysiologist to view the relative location of the distal end of the needle electrode, thereby providing both evidence concerning adequate tissue penetration and reassurance that the needle electrode has not penetrated all the way through the myocardium into the pericardium. The contrast agent also gives the electrophysiologist an indication of the approximate size and shape of the lesion that will be created.

The flowrate of the fluid through the needle ablation assembly and the duration of infusion can vary depending on the desired lesion size and the size of the distal tubing of the needle, i.e., that part of the needle introduced into the tissue. For example, saline or other fluid can be infused through the needle ablation assembly into the heart tissue at a rate ranging from about 0.3 to about 5 ml/min, more particularly from about 0.3 to about 3 ml/min, still more particularly from about 0.8 to about 2.5 ml/min, still more particularly from about 1 to about 2 ml/min. If infusing prior to ablation, preferably the fluid is not infused for more than a minute prior to beginning ablation.

Ablation energy, preferably radio frequency, is then applied to the distal tubing 35 of the ablation needle assembly 46 though the needle electrode lead wire 210. The amount of energy can vary depending on the desired lesion size, and can be, for example, up to about 100 watts, more particularly up to about 70 watts, still more particularly from about 20 to about 50 watts, even more particularly from about 30 to about 40 watts. The duration of the ablation, i.e., the duration that the radio frequency energy is delivered to the needle electrode and thus to an area of tissue through the needle electrode and through the saline or other fluid passing through the needle electrode, can also vary on the size of the desired lesion. It has been found that substantial lesions can be created with a duration of ablation that need not be significantly longer than about 120 seconds. Preferably the duration of ablation is at least about 15 seconds, more preferably at least about 30 seconds, and may last as long as 60 seconds, 90 seconds or more.

If the needle electrode is used for ablation without prior or simultaneous fluid of an ionically-conductive fluid, the lesion size will not be as large, and the amount of power cannot be as high as with the infusion of the fluid. For example, for a needle electrode without saline infusion, the power should not exceed about 5 to 10 watts to avoid charring, whereas much more power can be delivered with fluid infusion without significant charring. The saline or other fluid permeates between the muscle fibers and spreads out from the needle electrode puncture site. As a result, the electrical resistance is spread over a larger area. The resulting lesion is typically generally spherically-shaped.

If desired, a surface lesion can be burned with the tip electrode 32 before, during and/or after a lesion is created with the needle electrode to increase the size of the endocardial portion of the ablation and create a more bullet-shaped lesion. In an alternative method, the needle electrode is used only to infuse saline into the heart tissue, and the tip electrode is the used to ablate a burn from the tissue surface.

Impedance can be measured through the needle electrode, for example, by the radio frequency energy generator, as is generally known in the art. The impedance measurement can be used to vary the flow rate of the saline or other fluid, the amount of power delivered, and/or the time that the fluid is infused and/or the power delivered. If desired, a feedback control loop can be created.

Similarly, the temperature of the tissue can be indirectly measured by measuring the temperature of the distal tubing 35 of the ablation needle assembly 46 using the temperature sensor mounted in the distal tubing. The temperature measurement can similarly be used to vary the flow rate of the saline or other fluid, the amount of power delivered, and/or the time that the fluid is infused and/or the power delivered, and a feedback control loop can be created. Preferably the temperature of the distal tubing 35 ranges from about 35 to about 90° C., more preferably from about 45 to about 80° C., still more preferably from about 55 to 70° C. If desired, a portion of the distal tubing 35 of the needle ablation assembly 46 can be coated or covered with an insulating material. Preferably the distal end region, e.g., about 1 to about 30 mm, more particularly from about 2 to about 20 mm, even more particularly from about 3 to about 12 mm, of the distal tubing 35 is exposed, i.e., remains electrically conductive, and a region proximal to the distal end region is covered with the insulating material. With this design, ablation energy can be delivered to the tissue without being delivered at the endocardial surface to avoid overheating at the endocardial surface, which can cause clotting.

The distal tubing 35 of the needle ablation assembly 46, the tip electrode 32 and/or any ring electrodes 38 can be used to measure and record electrical activity. In particular, the electrical activity can be measured before ablation to confirm that the tissue should be ablation and/or after ablation to confirm that the ablation had the desired effect on the tissue, e.g., that the electrical activity in that tissue has been changed or eliminated. The distal tubing 35 of the needle ablation assembly 46 and/or the tip electrode 32 can also be used for pacing, for example, to determine whether tissue is viable before ablating and/or to determine whether the ablation had the desired effect.

EXAMPLES

The following examples show suitable ablation methods according to the invention. Experiments were conducted in vitro using bovine myocardium, and in vivo using swine and goats.

Example 1

In Vitro Needle Ablation Studies

Figure 9:
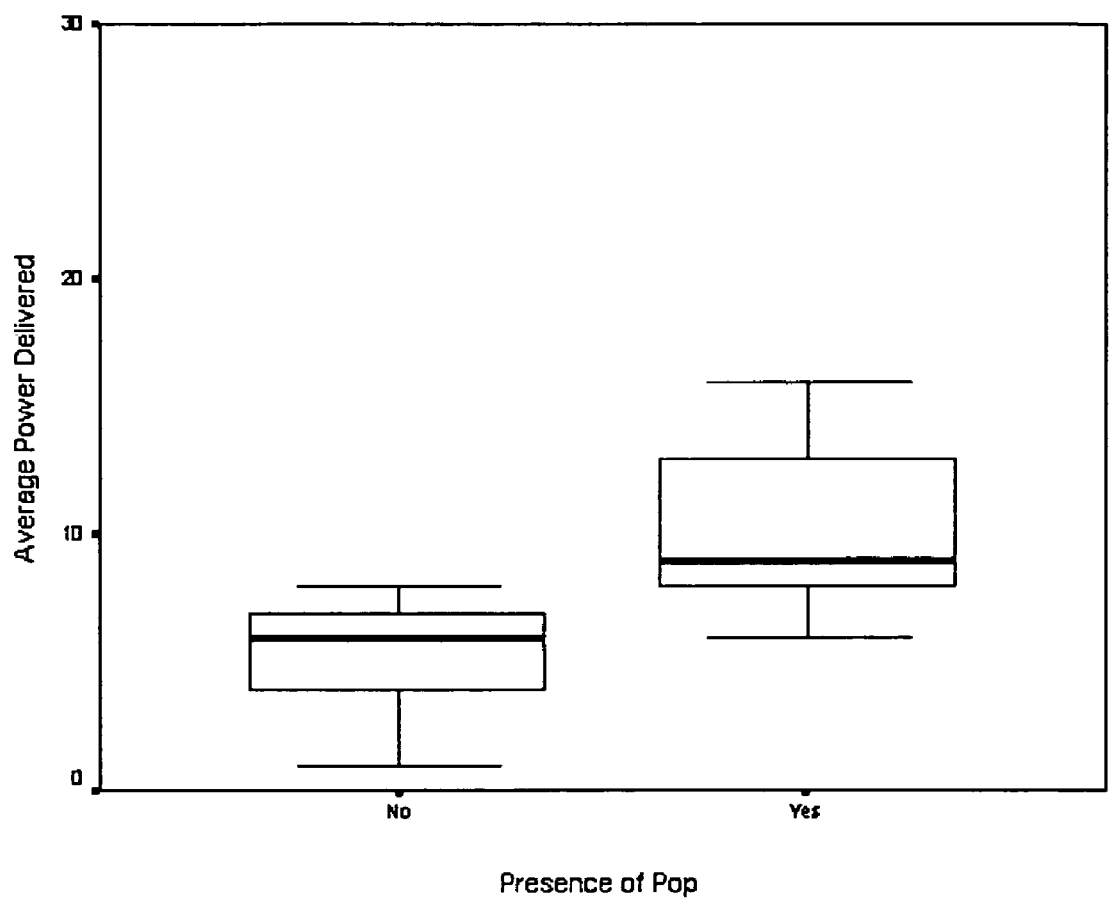
FIG. 9 is a graph showing the presence of pops versus power delivered to tissue in vitro using a catheter having a needle electrode as described in Example 1.
Figure 10:
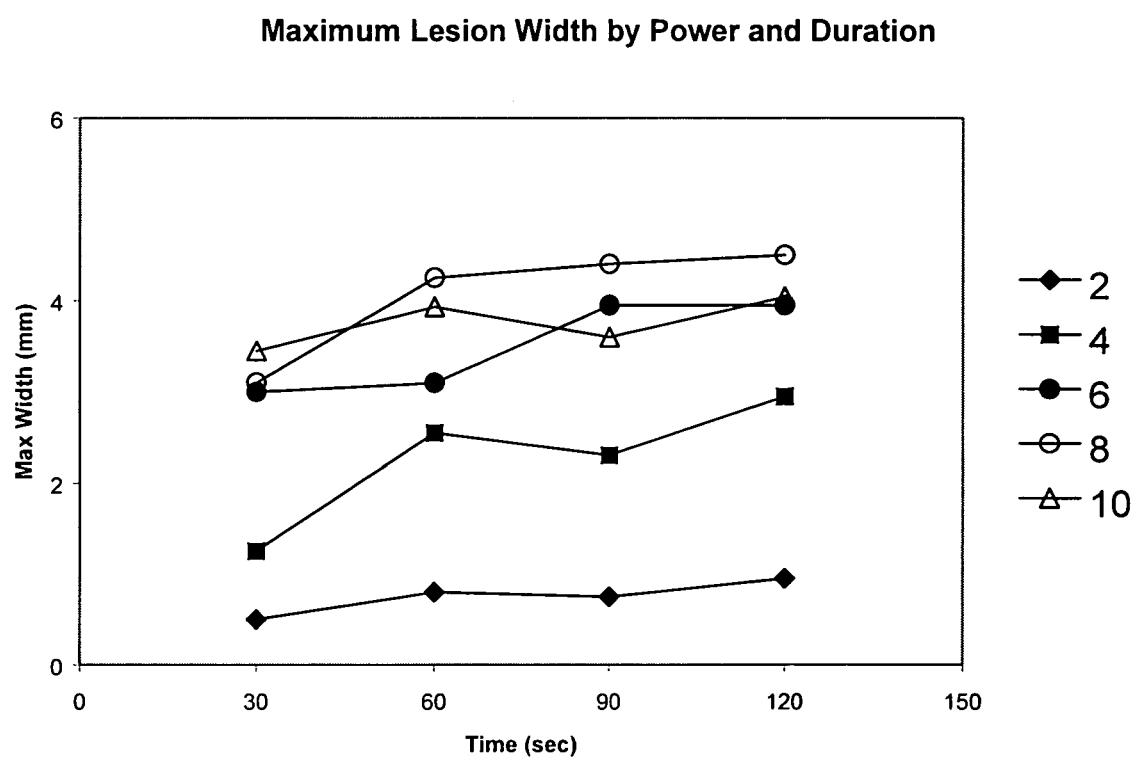
FIG. 10 is a graph showing maximum lesion width by power and duration for lesions created in vitro using a catheter having a needle electrode as described in Example 1.

Feasibility studies of delivery of radiofrequency (RF) ablative energy to tissue using a catheter having a needle electrode were carried out using bovine myocardium in room temperature 0.9% NaCl solution. RF energy was delivered using a Stockert 70 RF generator. Tissue overheating and pops occurred at relatively low power outputs. Steam pops tended to occur when power was higher, but this did not reach statistical significance (p=0.183). See FIG. 9. It was determined that lesions could be created and had depth to the full extent of needle penetration, but lesion diameter was limited by impedance rises and tissue overheating, with subsequent current limitation. RF lesion diameter increased with average power delivered and with maximum power delivered. Lesion size plateaued after 30 to 60 seconds of RF application, and increased with power delivered, reaching a plateau at 8 to 10 Watts. See FIG. 10. Lesion depth was limited only by needle length.

Example 2

In Vivo Needle Ablation Studies

Figure 11:
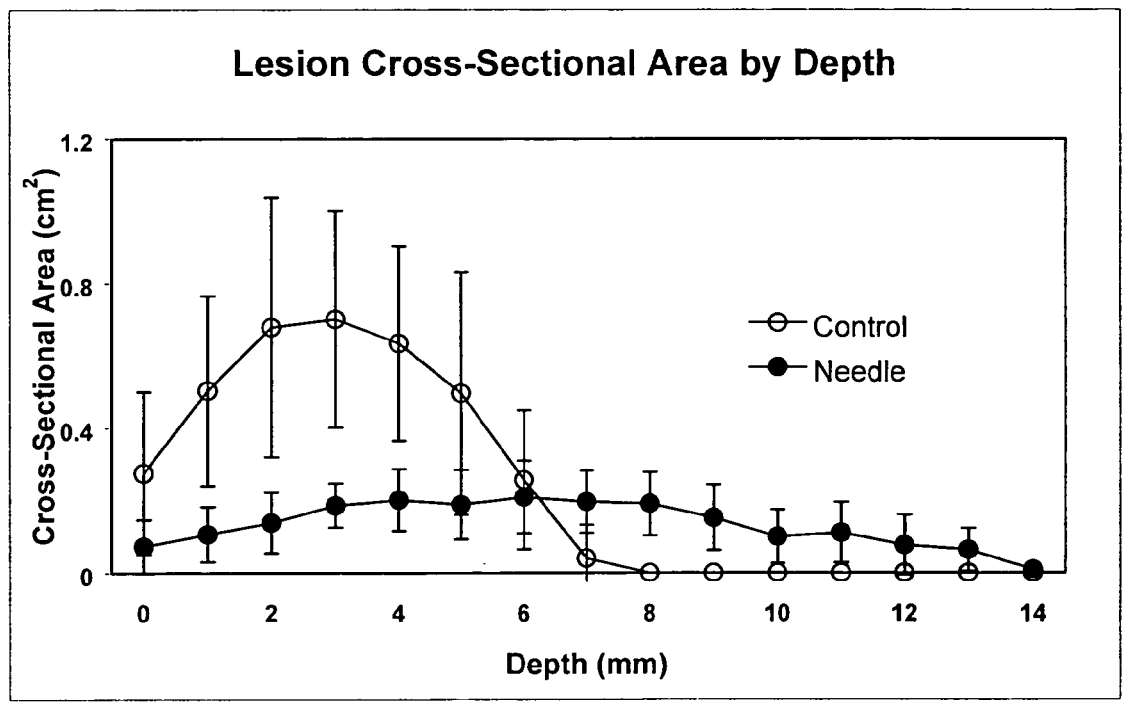
FIG. 11 is a graph showing lesion cross-sectional area by depth for lesions created in vivo using a catheter having a needle electrode as described in Example 2.

In vivo temperature-controlled needle ablation lesions were performed in anaesthetized swine. The catheter was introduced into femoral vessels and navigated using fluoroscopy and electroanatomic mapping. The distal end was placed in contact with and perpendicular to the endocardium. The needle electrode was extended 10 mm, and RF energy (500 kHz, Stockert-70 RF Generator, Freiburg, Germany) was delivered between the needle electrode and a skin electrode for 120 second applications. Temperature was monitored using the thermocouple within the needle electrode, and power was titrated manually to maintain temperature at or below 90° C. Control lesions were created with a standard ablation catheter under temperature control titrated to maintain tip temperature at or below 60° C. for 120 second applications. Thirteen needle ablations and nine control lesions were available for analysis. The animal was sacrificed, and the lesions were identified and excised. They were formalin-fixed and serially sectioned from the endocardium and digitally imaged for quantitative analysis. Needle ablation lesions had a characteristic appearance with minimal endocardial disruption, and a small circular area of pallor. The cut surfaces revealed a long narrow lesion extending the full length of the needle track with a uniform diameter. Control lesions had an ovoid area of pallor on the surface, slight widening within the first 2 mm of depth, and then rapid tapering. Needle lesions were significantly deeper than control lesions but of smaller volume. See Table 1, below, and FIG. 11.

TABLE 1

In Vivo Needle Ablation Results

| | Needle Lesions | Control Lesions | |
|---|---|---|---|
| Mean Depth | 10.2 ± 0.8 mm | 5.7 ± 0.4 mm | p < 0.001 |
| Likelihood Transmural | 77% | 11% | p = 0.008 |
| Mean Volume | 175 ± 18 mm$^3$ | 358 ± 56 mm$^3$ | p = 0.02 |
| Maximal Diameter (mean) | 7 ± 0.4 mm | 12 ± 0.7 mm | p < 0.001 |

Example 3

In Vitro Needle Infusion Ablation Studies

Figure 12:
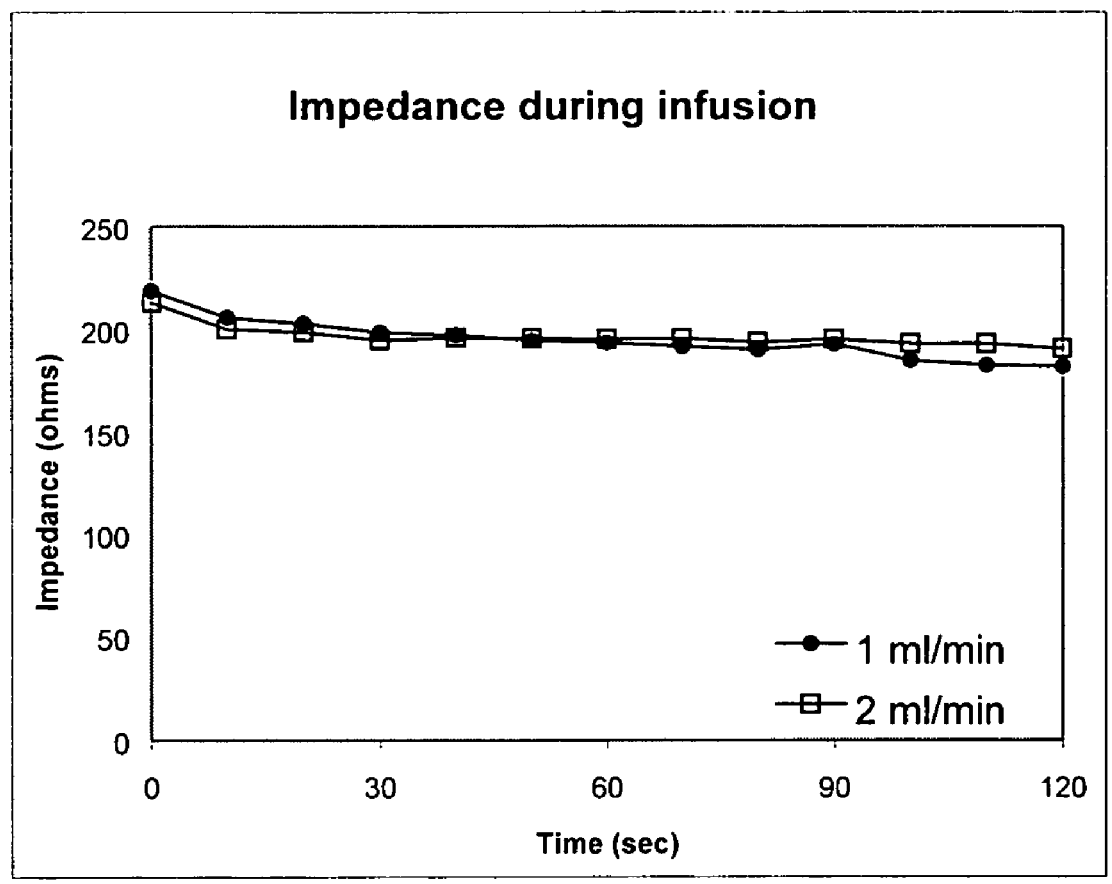
FIG. 12 is a graph showing impedance during infusion of ionic solution through the needle electrode in vitro as described in Example 3.

In order to increase lesion dimension, the size of the area of resistive heating needed to be increased. Infusion of ionic solution through the needle electrode into the tissue of interest increased the size of the virtual electrode, increasing conductance in the area immediately surrounding the ablating needle electrode. This shifts the site of the steepest gradient of resistance, and thus the zone of resistive heating farther from the electrode and creates a larger area of resistive heating, and consequently a larger area of conductive heating. Bovine myocardium strips were immersed in ionic solution at room temperature. The needle electrode was deployed within the tissue, and 0.9% NaCl solution was infused at 1 mL/minute and 2 mL/minute with serial observations of the impedance recorded. The initial impedance fell by approximately 20 ohms during the first 20 seconds of infusion and then relatively plateaued during the rest of 120 seconds of infusion. See FIG. 12.

Figure 13:
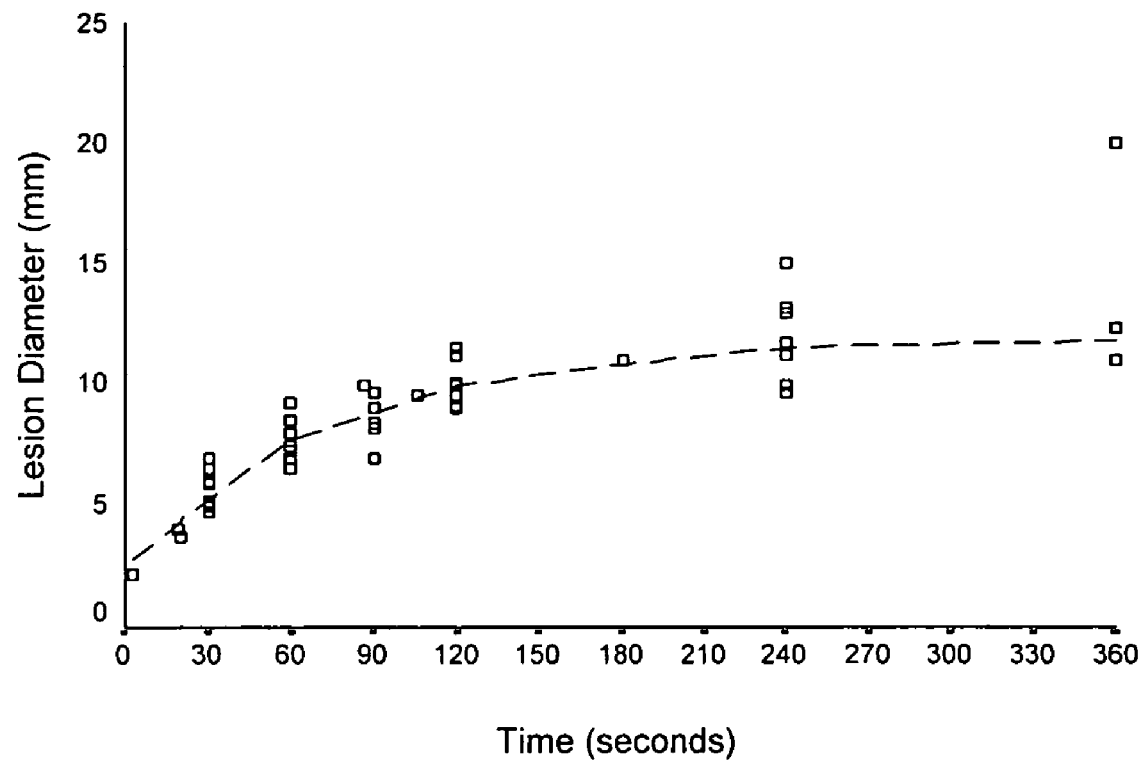
FIG. 13 is a graph showing lesion diameter over time of ablation for lesions created using a needle electrode with saline infusion in vitro as described in Example 3.

Further studies demonstrated in vitro that with a preinjection of 0.9% NaCl of up to 60 seconds at 1 mL/min, and with continued 1 mL/min infusion during RF and power set at 10 W, lesion size plateaued at approximately 120 seconds. Lesions created in this manner were significantly larger than those created without saline infusion. See FIG. 13.

Example 4

In Vivo Needle Infusion Ablation Studies

Figure 14:
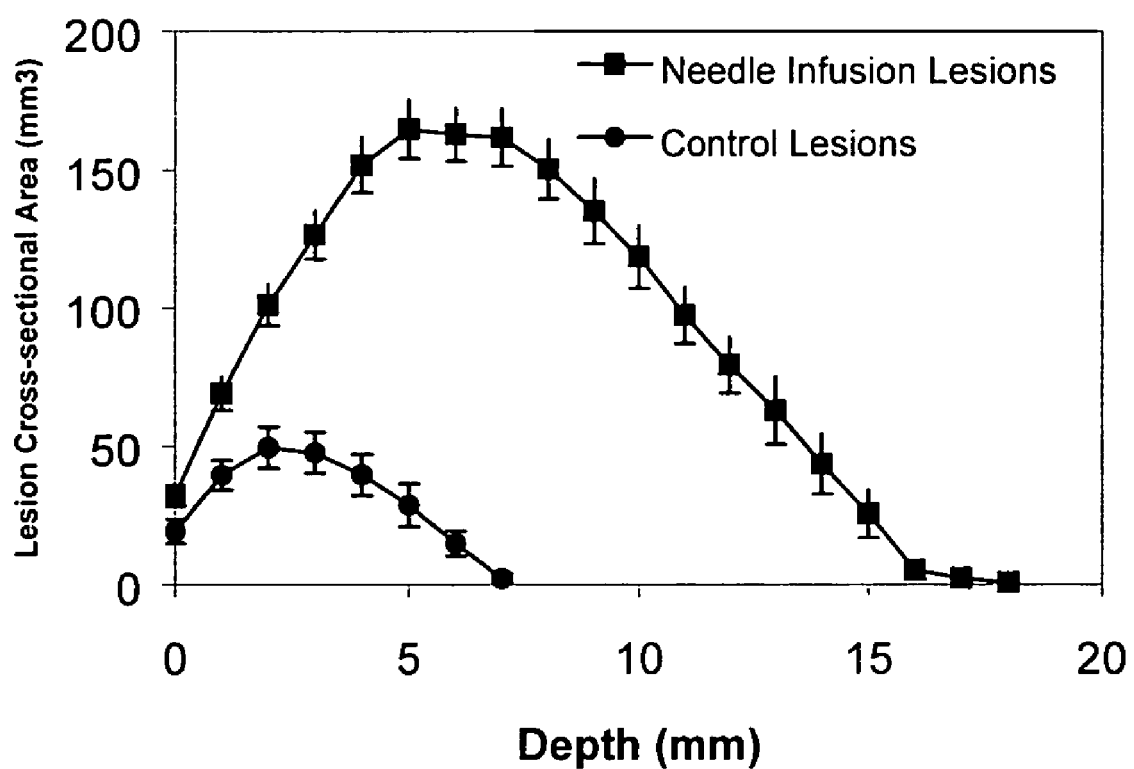
FIG. 14 is a graph showing lesion cross-sectional area versus depth for lesions created using a needle electrode with saline infusion in vivo as described in Example 4.

In ten anaesthetized swine, the left ventricle was entered using the catheter via the femoral artery and directed using electroanatomic mapping and fluoroscopy. The distal end of the catheter was positioned perpendicularly to the endocardial surface, and the needle electrode was advanced 5 to 7 mm into the myocardium. 0.9% NaCl solution was infused at 1 mL/min intramyocardially for 60 seconds, and RF was delivered via the needle electrode for 120 seconds during ongoing infusion. Power was titrated to 30 to 40 Watts, adjusted to avoid impedance rises. At the end of the procedure, the heart was excised, and the lesions were identified, excised and formalin fixed. They were then serially sectioned from the endocardium and digitally imaged for quantitative analysis. Lesion volume was calculated. Lesions were compared to standard endocardial ablation lesions created under power control, titrated to achieve a 10 ohm impedance fall using a 4 mm tip catheter. Needle infusion ablation lesions were significantly deeper than controls, more likely to be transmural and had significantly larger volumes and cross-sectional areas at each millimeter of depth beyond the endocardium. See Table 2 and FIG. 14.

TABLE 2

Saline Needle Infusion In Vivo

| | Needle/Infusion | Control | |
|---|---|---|---|
| Mean Depth | 13 ± 2 mm | 5 ± 1 mm | P < 0.001 |
| Likelihood Transmural | 41% | 11% | P = 0.03 |
| Volume | 1600 ± 100 mm$^3$ | 240 ± 40 mm$^3$ | P < 0.001 |

The preceding description has been presented with reference to presently preferred embodiments of the invention. Workers skilled in the art and technology to which this invention pertains will appreciate that alterations and changes in the described structure may be practiced without meaningful departing from the principal, spirit and scope of this invention. For example, the tip electrode can be eliminated if desired. The location sensor could also be eliminated, in which case another mapping method, such as ultrasound, could optionally be used to determine the location of the catheter. Accordingly, the foregoing description should not be read as pertaining only to the precise structures and methods described and illustrated in the accompanying drawings, but rather should be read consistent with and as support to the following claims which are to have their fullest and fair scope.

The invention claimed is:

1. A method for ablating tissue in or around the heart comprising:

introducing into the heart a distal end of a catheter comprising a catheter body and, a needle electrode assembly at the distal end of the catheter body, the needle electrode assembly comprising a proximal tubing and distal tubing, wherein the proximal tubing is more flexible than the distal tubing, the distal tubing of the needle electrode assembly being in a retracted position within the distal end of the catheter;

introducing a distal end of the distal tubing of the needle electrode assembly into the tissue, including moving the distal tubing of the needle electrode assembly from its retracted position within the distal end of the catheter to an extended position outside the distal end of the catheter;

infusing into the tissue an electrically-conductive fluid through the distal tubing of the needle electrode assembly while in the extended position; and ablating the tissue after and/or during introduction of the fluid into the tissue, whereby the fluid conducts ablation energy within the tissue to create a larger lesion than would be created without the introduction of the fluid.

2. The method according to claim 1, wherein the tissue is ablated using the distal tubing of the needle electrode assembly.

3. The method according to claim 2, wherein radio frequency energy is delivered to the distal tubing of the needle electrode assembly for the ablation.

4. The method according to claim 1, wherein the tissue is ablated using a tip electrode on the distal end of the catheter.

5. The method according to claim 1, wherein a portion of the distal tubing of the needle electrode assembly that is introduced into the tissue has an insulating coating.

6. The method according to claim 5, wherein the insulating coating is over a portion of the distal tubing of the needle electrode assembly that is in contact with the endocardial surface of the tissue being ablated.

7. The method according to claim 1, wherein the distal tubing of the needle electrode assembly comprises nitinol.

8. The method according to claim 1, wherein the distal tubing of the needle electrode assembly is introduced to a depth ranging from about 2 to about 30 mm.

9. The method according to claim 1, wherein the distal tubing of the needle electrode assembly is introduced to a depth ranging from about 4 to about 10 mm.

10. The method according to claim 1, wherein the distal tubing of the needle electrode assembly is introduced to a depth ranging from about 3 to about 20 mm.

11. The method according to claim 1, wherein the distal tubing of the needle electrode assembly is introduced to a depth ranging from about 5 to about 7 mm.

12. The method according to claim 1, wherein fluid is infused through the distal tubing of the needle electrode assembly during ablation.

13. The method according to claim 1, wherein fluid is infused through the distal tubing of the needle electrode assembly before ablation.

14. The method according to claim 1, wherein fluid is infused through the distal tubing of the needle electrode assembly before and during ablation.

15. The method according to claim 1, wherein the fluid infused through the distal tubing of the needle electrode assembly comprises saline having a salt content ranging from about 0.3 to about 4 wt%.

16. The method according to claim 1, wherein the fluid infused through the distal tubing of the needle electrode assembly comprises saline having a salt content ranging from about 0.5 to about 3 wt%.

17. The method according to claim 1, wherein the fluid infused through the distal tubing of the needle electrode assembly comprises saline having a salt content ranging from about 0.9 to about 2.5 wt%.

18. The method according to claim 1, wherein the fluid infused through the distal tubing of the needle electrode assembly comprises saline having a salt content ranging from about 1.5 to about 2 wt%.

19. The method according to claim 1, wherein the fluid infused through the distal tubing of the needle electrode assembly comprises a radiographic contrast agent.

20. The method according to claim 19, wherein the amount of contrast agent present in the fluid ranges from about 5 to about 50%.

21. The method according to claim 19, wherein the amount of contrast agent present in the fluid ranges from about 10 to about 30%.

22. The method according to claim 19, wherein the amount of contrast agent present in the fluid ranges from about 10 to about 20%.

23. The method according to claim 1, wherein the fluid is infused through the distal tubing of the needle electrode assembly at a rate ranging from about 0.3 to about 5 ml/mm.

24. The method according to claim 1, wherein the fluid is infused through the distal tubing of the needle electrode assembly at a rate ranging from about 0.3 to about 3 ml/mm.

25. The method according to claim 1, wherein the fluid is infused through the distal tubing of the needle electrode assembly at a rate ranging from about 0.8 to about 2.5 ml/mm.

26. The method according to claim 1, wherein the fluid is infused through the distal tubing of the needle electrode assembly at a rate ranging from about 1 to about 2 ml/min.

27. The method according to claim 3, wherein radiofrequency energy is introduced to the distal tubing of the needle electrode assembly at a power of up to about 70 watts.

28. The method according to claim 3, wherein radiofrequency energy is introduced to the distal tubing of the needle electrode assembly at a power ranging from about 20 to about 50 watts.

29. The method according to claim 3, wherein radiofrequency energy is introduced to the distal tubing of the needle electrode assembly at a power ranging from about 30 to about 40 watts.

30. The method according to claim 3, wherein radiofrequency energy is introduced to the distal tubing of the needle electrode assembly for at least about 15 seconds.

31. The method according to claim 3, wherein radiofrequency energy is introduced to the distal tubing of the needle electrode assembly for at least about 30 seconds.

32. The method according to claim 3, wherein radiofrequency energy is introduced to the distal tubing of the needle electrode assembly for at least about 60 seconds.

33. The method according to claim 2, further comprising burning a surface lesion with a tip electrode on the catheter, wherein the surface lesion is burned at the endocardial surface of the tissue ablated with the distal tubing of the needle electrode assembly.

34. The method according to claim 1, further comprising taking an impedance measurement using the distal tubing of the needle electrode assembly before, during and/or after introduction of the distal end of the distal tubing of the needle electrode assembly into the tissue.

35. The method according to claim 34, further comprising adjusting the flow rate of the fluid infused through the distal tubing of the needle electrode assembly, an amount of power delivered to the distal tubing of the needle electrode assembly, and/or the time over which the fluid is infused and/or the power delivered in response to the impedance measurement.

36. The method according to claim 1, further comprising measuring the temperature of the distal tubing of the needle electrode assembly during ablation.

37. The method according to claim 36, further comprising adjusting the flow rate of the fluid infused through the distal tubing of the needle electrode assembly, an amount of power delivered to the distal tubing of the needle electrode assembly, and/or the time over which the fluid is infused and/or the power delivered in response to the temperature measurement.

38. The method according to claim 37, wherein the distal tubing of the needle electrode assembly is maintained at a temperature ranging from about 35 to about 900 C.

39. The method according to claim 37, wherein the distal tubing of the needle electrode assembly is maintained at a temperature ranging from about 45 to about 800 C.

40. The method according to claim 37, wherein the distal tubing of the needle electrode assembly is maintained at a temperature ranging from about 55 to about 700 C.

41. The method according to claim 1, further comprising measuring electrical activity using the distal tubing of the needle electrode assembly before and/or after ablation.

42. The method according to claim 1, further comprising pacing using the distal tubing of the needle electrode assembly before and/or after ablation.

* * * * *

UNITED STATES PATENT AND TRADEMARK OFFICE
CERTIFICATE OF CORRECTION

PATENT NO. : 7,207,989 B2  Page 1 of 1
APPLICATION NO. : 10/694118
DATED : April 24, 2007
INVENTOR(S) : Pike, Jr. et al.

It is certified that error appears in the above-identified patent and that said Letters Patent is hereby corrected as shown below:

In the Claims

Column 17, line 19, Claim 23  Delete "5 ml/mm",
Insert --5 ml/min--

Column 17, line 22, Claim 24  Delete "3 ml/mm",
Insert --3 ml/min--

Column 17, line 26, Claim 25  Delete "ml/mm",
Insert --ml/min--

Column 18, line 32, Claim 38  Delete "900 C",
Insert --90°C--

Column 18, line 35, Claim 39  Delete "800 C",
Insert --80°C--

Column 18, line 38, Claim 40  Delete "700 C",
Insert --70°C--

Signed and Sealed this

Eighteenth Day of March, 2008

JON W. DUDAS
*Director of the United States Patent and Trademark Office*